(12) United States Patent  
Paik et al.

(10) Patent No.: US 7,616,800 B2
(45) Date of Patent: Nov. 10, 2009

(54) POLYP IDENTIFICATION THROUGH SUBTRACTION OF MODELS OF MEDICAL IMAGES

(75) Inventors: David S. Paik, Half Moon Bay, CA (US); Padmavathi Sundaram, Palo Alto, CA (US); Christopher F. Beaulieu, Los Altos, CA (US); Sandy A. Napel, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 17 days.

(21) Appl. No.: 11/666,202

(22) PCT Filed: Nov. 8, 2005

(86) PCT No.: PCT/US2005/040627

§ 371 (c)(1),
(2), (4) Date: Apr. 9, 2008

(87) PCT Pub. No.: WO2006/053065

PCT Pub. Date: May 18, 2006

(65) Prior Publication Data

US 2008/0310693 A1 Dec. 18, 2008

Related U.S. Application Data

(60) Provisional application No. 60/626,260, filed on Nov. 8, 2004.

(51) Int. Cl.
*G06T 17/40* (2006.01)

(52) U.S. Cl. .................. 382/131; 382/154; 345/419

(58) Field of Classification Search ............. 382/128, 382/130, 131, 154, 173; 345/419, 423, 424
See application file for complete search history.

(56) References Cited

U.S. PATENT DOCUMENTS

| 6,496,188 | B1 | 12/2002 | Deschamps et al. | 345/419 |
|---|---|---|---|---|
| 2004/0264778 | A1 | 12/2004 | Liang et al. | 382/203 |
| 2005/0078858 | A1* | 4/2005 | Yao et al. | 382/128 |
| 2005/0107691 | A1 | 5/2005 | Zalis | 600/425 |
| 2005/0117787 | A1* | 6/2005 | Iordanescu et al. | 382/128 |
| 2005/0163356 | A1* | 7/2005 | Makram-Ebeid et al. | 382/128 |
| 2008/0089569 | A1* | 4/2008 | Sundaram et al. | 382/131 |

OTHER PUBLICATIONS

Deschapms, Thomas et al. "Fast Extraction of Tubular and Tree 3D Surface With Front Propagation Methods" (2002) 16th International Conference on Pattern Recognition, Quebec, Canada.

* cited by examiner

*Primary Examiner*—Andrew W Johns
(74) *Attorney, Agent, or Firm*—Lumen Patent Firm

(57) ABSTRACT

A method of identifying polyps and in a medical image is provided. In a first step, a 3-dimensional model is made of the medical image that contains both polyps (if any were present in the original medical image) and folds. Next, a second 3-dimensional model of the medical image, which is a filtered version of the first model, is constructed in which folds are preserved, but polyps are minimized or eliminated. In a third step, any polyps that were contained in the medical image are identified by subtracting the second 3-dimensional model from the first 3-dimensional model. This subtraction results in a third 3-dimensional model, in which polyps are preserved but folds are minimized or eliminated. With the present inventive method, polyps may be easily and quickly identified without interference from folds.

6 Claims, 5 Drawing Sheets

POLYP IDENTIFICATION THROUGH SUBTRACTION OF MODELS OF MEDICAL IMAGES

This application is the National Stage of International Application No. PCT/US2005/040627, filed Nov. 8, 2005, which claimed the benefit of Provisional Application No. 60/626,260, filed Nov. 8, 2004.

FEDERALLY-SPONSORED RESEARCH OR DEVELOPMENT

This invention was made with Government support under contracts CA072023 and HL067194 awarded by the National Institute of Health. The Government has certain rights in this invention.

FIELD OF THE INVENTION

The present invention relates generally to feature detection. More particularly, the present invention relates to the detection of polyps in the colon.

BACKGROUND

Colon cancer is the second leading cause of cancer deaths in the United States, with over 100,000 new cases and over 55,000 deaths expected in 2005. Traditionally, the colon surface is examined using colonoscopy, which involves the use of a lit, flexible fiberoptic or video endoscope to detect small lumps on the colon surface called polyps. Polyps are known to be precursors to colon cancer. Although colonoscopy provides a precise means of colon examination, it is an invasive procedure. Thus, colonoscopy is associated with a significant risk of injury to the colon and the possibility of colon perforation and peritonitis, which can be fatal.

A less invasive alternative to traditional colonoscopy is Computed Tomographic Colonography (CTC). CTC makes use of 2-dimensional images generated by computed tomography (CT) imaging systems, as well as 3-dimensional computer graphics renditions of the colonic surface using these images. A drawback of CTC is that radiologists must examine hundreds of 2-d images and/or 3-d renditions to detect polyps, which is very time consuming and can lead to inaccurate diagnoses.

Three-dimensional surface images rendered from an internal perspective ("virtual fly-through" or "virtual colonoscopy") appear similar to those produced by conventional colonoscopy. However, navigation through a tortuous, complex structure like the colon is challenging and, frequently, portions of the colonic surface may be missed, leading to incomplete examinations. Cylindrical and planar map projections have been proposed to increase the viewable surface during fly-through, but the presentation format is unfamiliar and the physician may still not have a complete view. Thus, there is a need in the art for methods of identifying polyps using CTC that are less time consuming, allow for more complete examination of the colonic surface, and allow for greater ease of identification of polyps than current methods.

SUMMARY OF THE INVENTION

The present invention provides a method of identifying polyps and other anatomic features in a medical image. The medical image may be an image of any organ that has folds and/or polyps, such as a colon, intestine, etc. According to the method of the present invention, the medical image would have zero or more polyps and at least one fold. In a first step of this method, a 3-dimensional model is made of the medical image that contains both polyps (if any were present in the original medical image) and folds. This first model may be any three-dimensional representation of the medical image that preserves polyps and folds, such as one constructed using wave front propagation. Next, a second 3-dimensional model of the medical image, which is a filtered version of the first model, is constructed in which folds are preserved, but polyps are minimized or eliminated. Any filter that preserves folds and minimizes or eliminates polyps may be used, such as a cubic spline filter. In a third step, any polyps that were contained in the medical image are identified by subtracting the second 3-dimensional model from the first 3-dimensional model. This subtraction results in a third 3-dimensional model, in which polyps are preserved but folds are minimized or eliminated. Any method of subtraction that results in minimized or eliminated folds and preserved polyps may be used to construct the third model. In one example, lines are constructed normal to the second model, the distances between the two models is calculated along these lines, and these distances are used to construct the third model. With the present inventive method, polyps may be easily and quickly identified without interference from folds. Thus, it can be easily determined whether a medical image has any polyps, and if so, the number of polyps contained in the medical image.

BRIEF DESCRIPTION OF THE FIGURES

The present invention together with its objectives and advantages will be understood by reading the following description in conjunction with the drawings, in which.

DETAILED DESCRIPTION OF THE INVENTION

Figure 1:
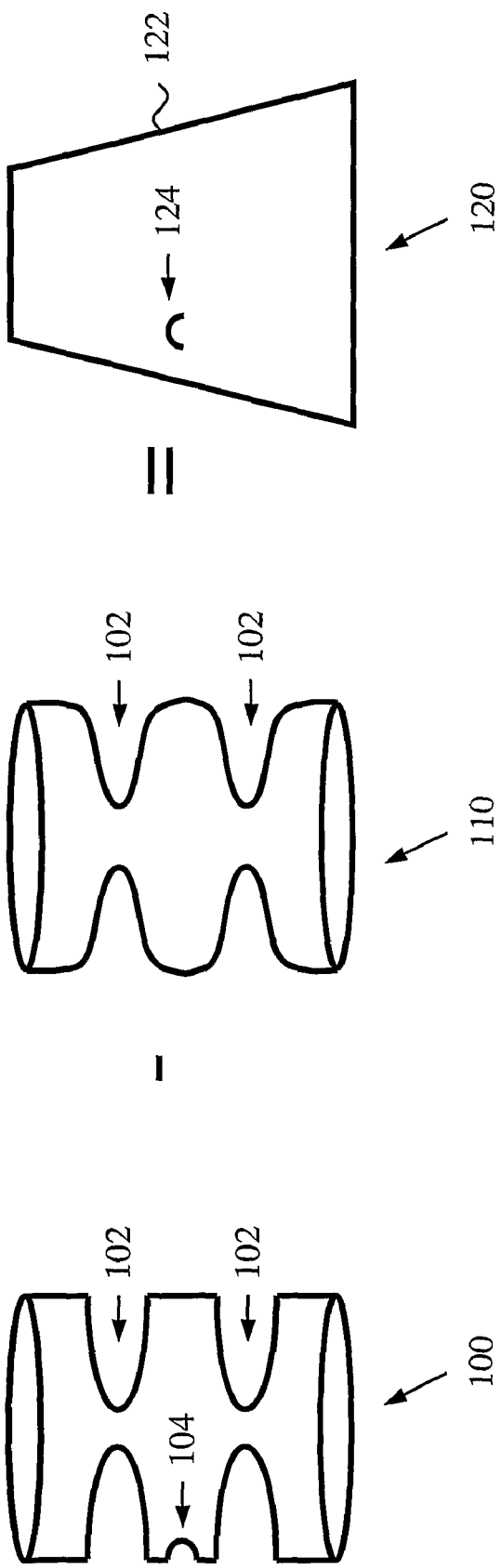
FIG. 1 shows a schematic of a method according to the present invention.

The present invention provides a method of identifying polyps and other anatomic features in a medical image having zero or more polyps and at least one fold by subtracting two different models of the medical image. In the example shown in FIG. 1, first model 100 of the medical image contains both folds 102 and polyp 104. In contrast, second model 110, which is a filtered version of first 3-dimensional model 110, contains folds 102 but not polyp 104. By subtracting second model 110 from first model 100, one can derive third model 120, which can be portrayed as a 3-dimensional flat surface 122, with vertical bump 124 representing polyp 104. Thus, polyp 104 can be easily detected from third model 120.

First model 100 is a 3-dimensional surface representation of the medical image that contains polyps and folds. First model 100 may be constructed using, e.g., surface wavefront propagation. A wavefront is created along the surface of the image such that the entire wavefront passes through each fold top at a single point in time. This is accomplished by solving the Eikonal equation ($|\nabla T|F=1$), where T is arrival time of the wavefront and F is the speed of propagation. The Eikonal equation can be solved using the Fast Marching method on a triangulated surface of the organ being imaged, e.g. the colon. However, this method satisfies a single boundary condition (i.e., location of the wavefront at a specified time), whereas for the purposes of this invention, there are dual boundary conditions to be satisfied. This is done by solving a forward wavefront propagation from the first boundary and a reverse wavefront propagation from the second boundary. The forward Eikonal equation is $|\nabla T_f|F=1$, where F=1, and the reverse Eikonal equation is $|\nabla T_r|F=1$, where F=1. The colon surface is separated into regions between the tops of successive folds, and the two Eikonal equations may be run separately within each fold-to-fold segment.

Figure 2:
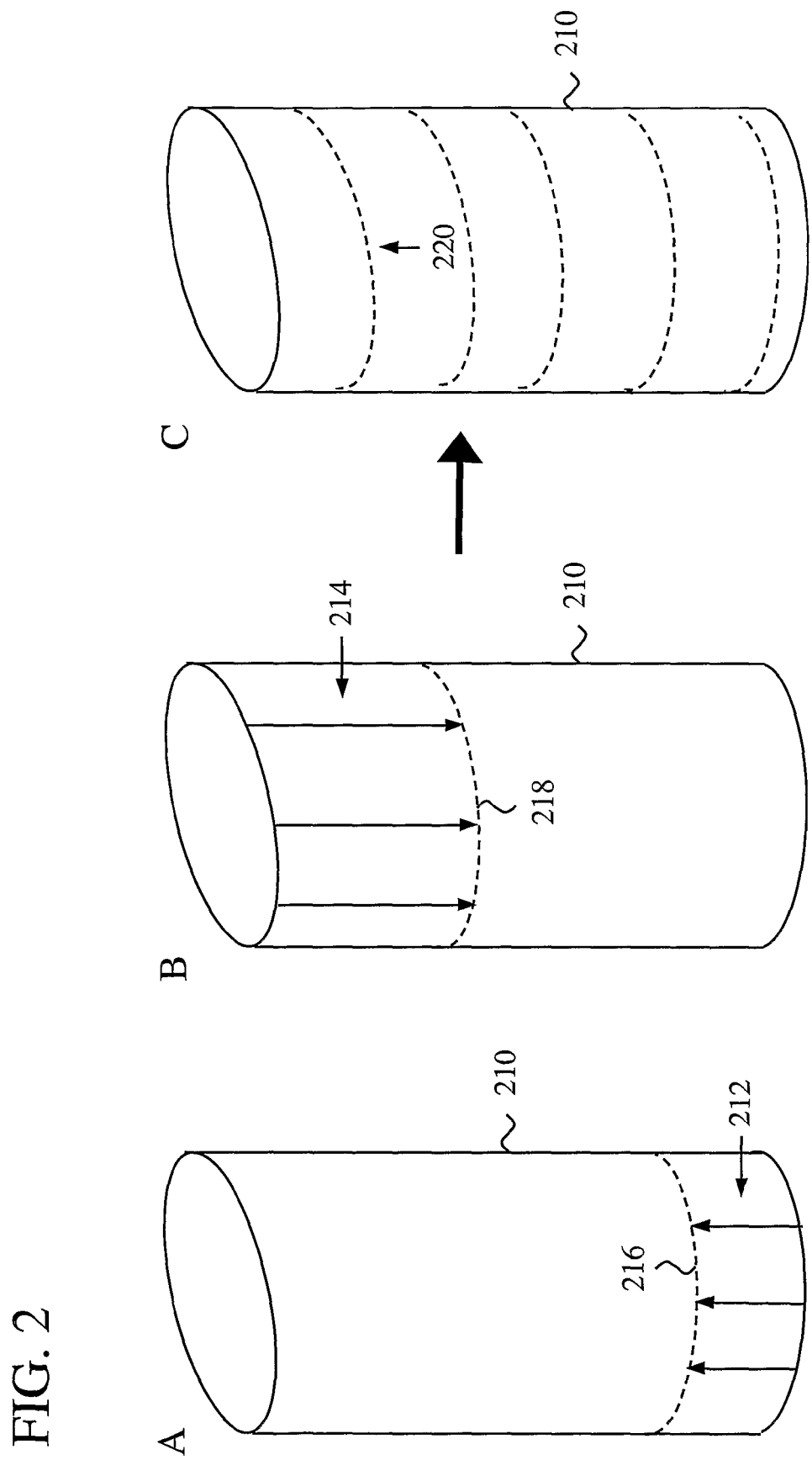
FIG. 2 shows wave front propagation according to the present invention.

FIG. 2 illustrates a segment of a colon with triangulated surface 210. The forward boundary condition for this segment (base of arrows 212), where $T_f=0$, is the distal (closer to the rectum) segment boundary. The reverse boundary condition for this segment (base of arrows 214), where $T_r=0$, is the proximal (closer to the cecum) segment boundary. FIG. 2A depicts the forward Eikonal equation, with the forward propagation of the wave indicated by arrows 212, and the wavefront indicated by dashed line 216. FIG. 2B depicts the reverse Eikonal equation, with the reverse propagation of the wave indicated by arrows 214, and the wavefront indicated by dashed line 218. Once the forward and reverse Eikonal equations are solved, level set functions of $T_f$ and $T_r$ are linearly interpolated to make T continuous from boundary to boundary (indicated by the series of dashed lines 220 in FIG. 2C). In particular, the new function, t, satisfies the relationship $(1-t)T_f-t^*T_r=0$, where t ranges from 0 to 1 in each segment. t* is a function that monotonically increases down the entire colon and is scaled according to the average segment length: $t^*_i = \bar{1} \cdot t_i + \max(t^*_{i-1})$, where i is the segment number and $1_i$ is the mean length of each segment. It is this function that is preferably used to construct the first model.

Figure 3:
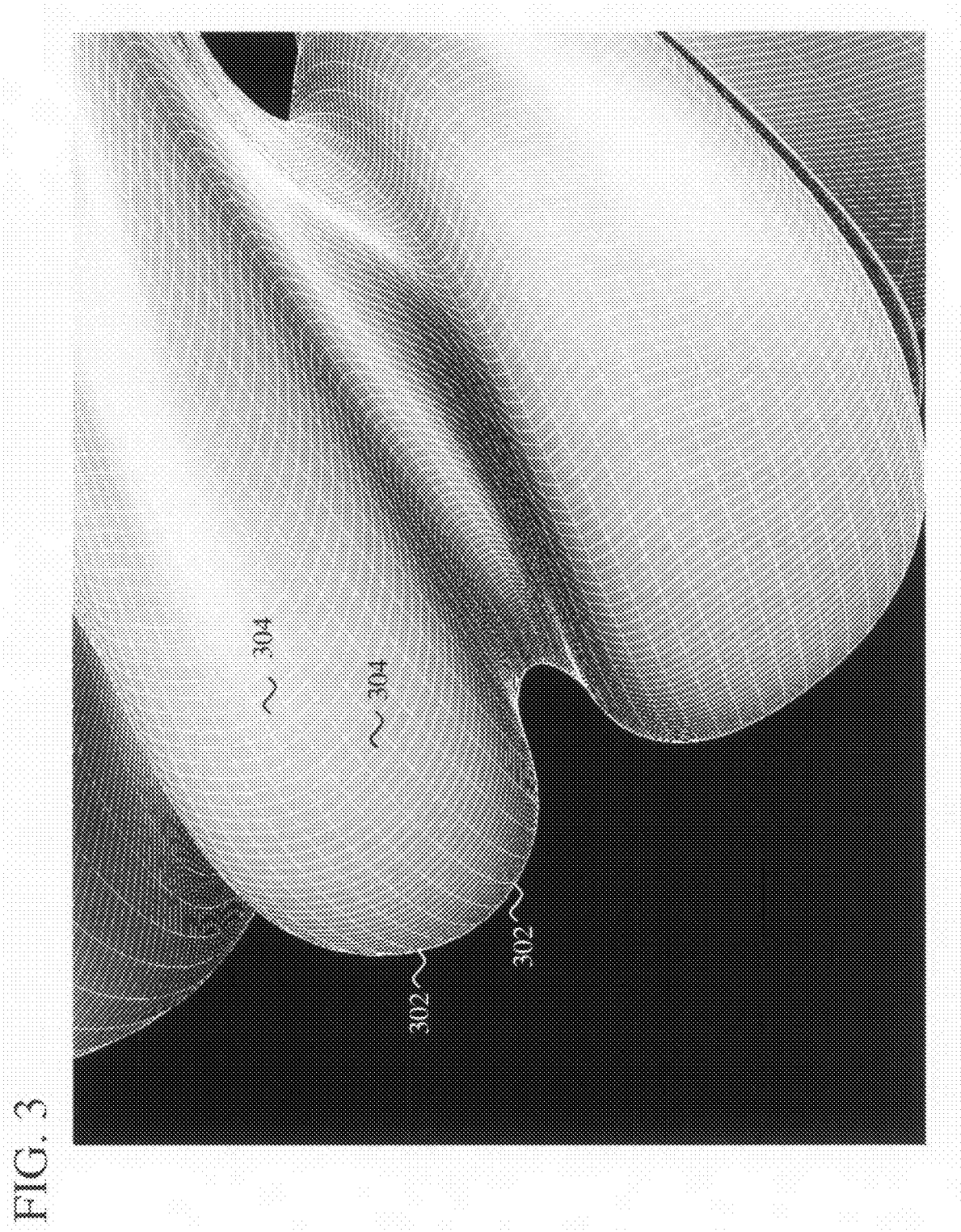
FIG. 3 shows a spline surface model according to the present invention.

The first 3-dimensional model is then filtered to obtain a second 3-dimensional model that has folds but in which polyps are minimized or eliminated. In one example, a spline surface could be used where a series of closed spline curves are defined by the t wavefronts. Preferably, about 8 to about 12 control points are used along isolevel contours of the wavefront to form each closed natural cubic spline (such as 302, FIG. 3). This number of control points has been demonstrated to be useful for ensuring that the general curve of the colon is retained, but bumps in the surface, such as polyps, are minimized or eliminated. Polyps are preferably minimized by about 50 to about 100%, more preferably minimized by about 85% to about 100%, and most preferably minimized by about 95 to about 100%. Lines in the longitudinal direction, such as 304, are created based on a gradient descent method, ensuring that the folds in the surface are accurately retained. Thus, a logically rectangular surface mesh is created by the longitudinal lines and the sequence of spline contours. This surface mesh retains folds found in the first model, but eliminates or minimizes polyps found in the first model.

Figure 4:
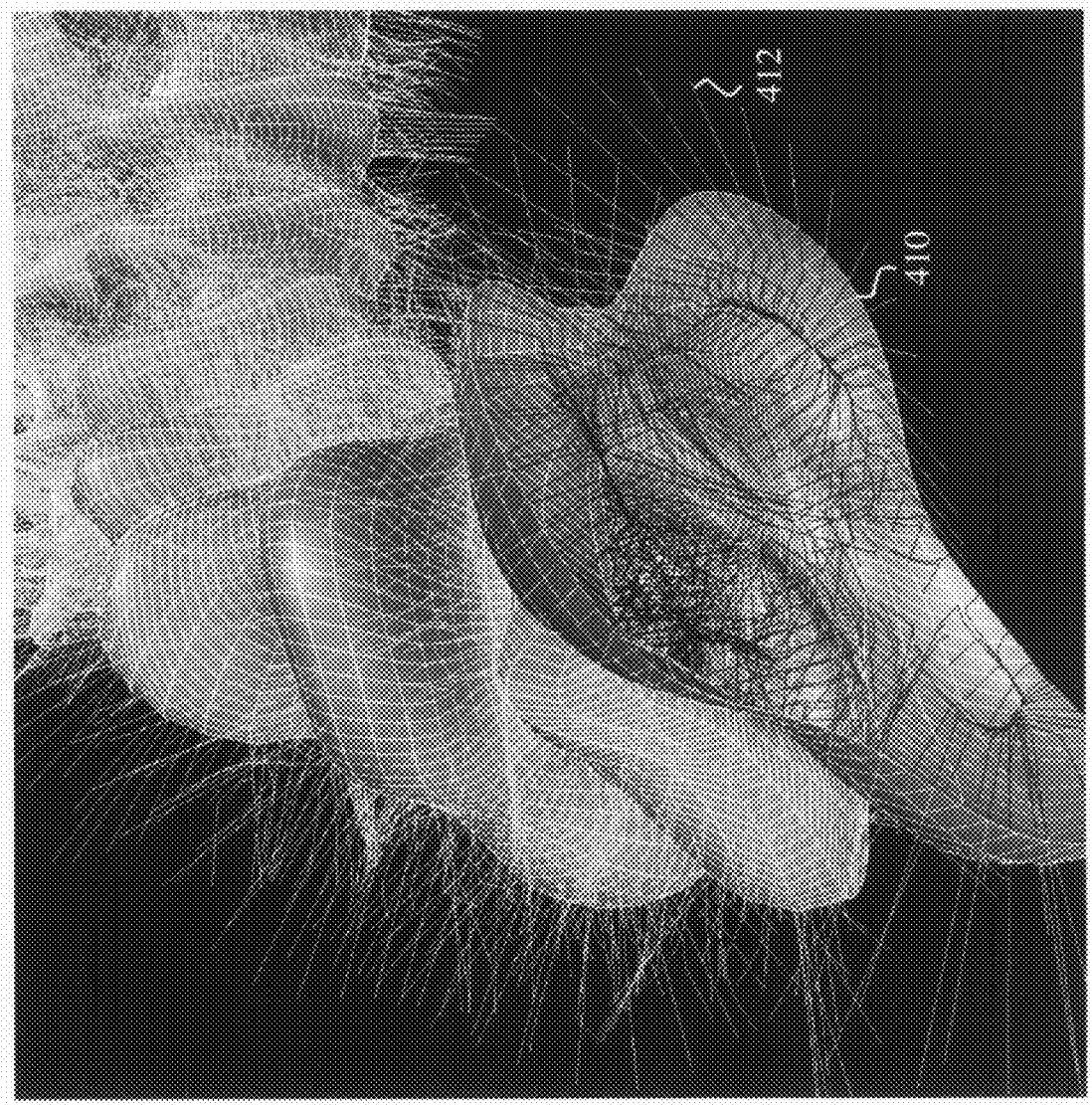
FIG. 4 shows subtraction of two models of a medical image according to the present invention.

In the next step, the second model is subtracted from the first model. This may be accomplished by first sampling inside and outside the mesh at each point along the rectangular surface mesh 410 (FIG. 4) of the second model. These sample lines 412 are allowed to curve, to avoid non-intuitive re-sampling artifacts. The sample lines, s, are generated by following a mixture of smooth mesh normals, $N_{u,v}$, and the original signed surface map $D_{x,y,z}$.

The following equations are the preferable method used in generating the sample lines:

$$\frac{d\check{s}}{dt} = (1 - f(\theta))\frac{\check{N}_{u,v}}{\|N_{u,v}\|} + f(\theta)\frac{\nabla \check{D}(\check{x})}{\|\nabla \check{D}(\check{x})\|}$$

$$\theta = a\cos\left(\check{s}' \frac{\nabla \check{D}(\check{x})}{\|\nabla \check{D}(\check{x})\|}\right)$$

$$f(\theta) = \begin{cases} 0 & \text{if } \theta < 80° \\ \frac{\theta - 80}{90 - 80} & \text{if } 80° < \theta \leq 90° \\ 1 & \text{if } \theta \geq 90° \end{cases}$$

At each point, the distance is then calculated along the line from the smoothed surface of the second model to the original surface of the first model. These distances are then used to construct a third model. This process will highlight differences in depth between the original and smoothed surfaces, and will therefore cause polyps to be visualized and folds to be minimized or eliminated. Preferably, this process minimizes folds by about 50 to about 100%, more preferably by about 75 to about 100% and most preferably by about 95 to about 100%.

Figure 5:
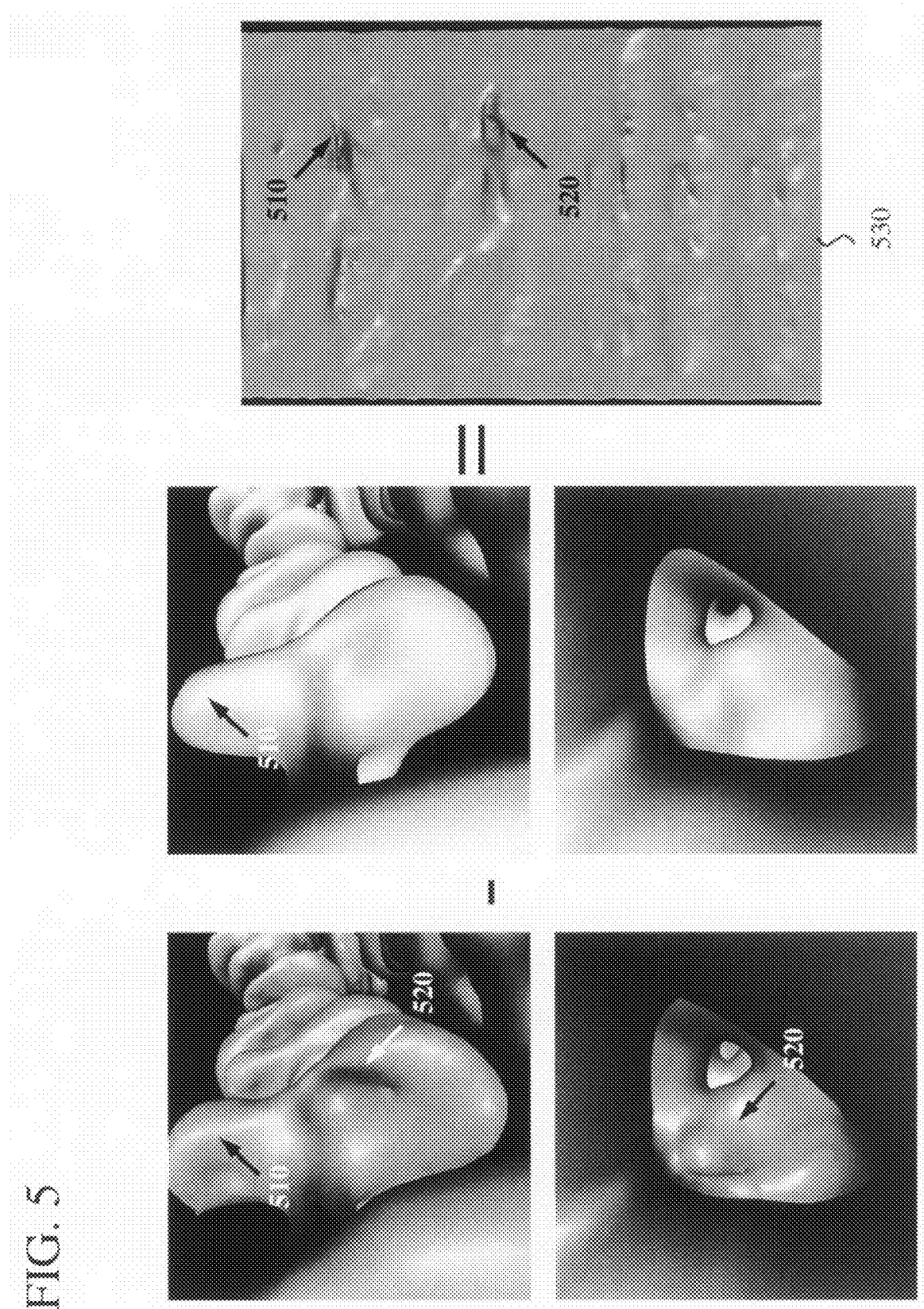
FIG. 5 shows an example of polyp identification using the method according to the present invention.

An example of the inventive method is shown in FIG. 5. FIG. 5A shows two views of a first surface model having both fold 510 and polyp 520. FIG. 5B shows the same two views of a second, smoothed, surface model. This model retains fold 510, but not polyp 520. FIG. 5C shows a third surface model, which was constructed by subtracting the second model from the first model. In this third surface model, polyp 520 is clearly visible as a depression in flat surface 530. Polyp 520 is easily distinguished from fold 510, which is observed as a slight crease in surface 530. Polyp 520 could be detected either manually or using computer-aided detection.

Although the present invention and its advantages have been described in detail, it should be understood that the present invention is not limited by what is shown or described herein. As one of ordinary skill in the art will appreciate, the unfolding methods disclosed herein could vary or be otherwise modified without departing from the principles of the present invention. Accordingly, the scope of the present invention should be determined by the following claims and their legal equivalents.

What is claimed is:

1. A method of identifying polyps in a medical image having at least one fold and zero or more polyps, comprising:
   (a) constructing a first 3-dimensional model of said medical image, wherein said first 3-dimensional model contains said at least one fold and said zero or more polyps contained in said medical image;
   (b) constructing a second 3-dimensional model of said medical image from said first 3-dimensional model, wherein said second 3-dimensional model contains said at least one fold but wherein said polyps are minimized or eliminated in the case where said first 3-dimensional model contains one or more of said polyps;
   (c) identifying said zero or more polyps by subtracting said second 3-dimensional model from said first 3-dimensional model, wherein said subtracting minimizes or eliminates said at least one fold.

2. The method as set forth in claim 1, wherein said first 3-dimensional model is constructed using wave front propagation.

3. The method as set forth in claim 1, wherein said second 3-dimensional model is a splined surface model of said first 3-dimensional model.

4. The method as set forth in claim 1, wherein said subtracting comprises:
   (a) constructing lines normal to a surface of said first model;
   (b) calculating the distances between said second model and said first model along said lines;
   (d) constructing a third 3-dimensional model based on said distances.

5. The method, as set forth in claim one, wherein said medical image is a computed tomographic image.

6. The method as set forth in claim one, wherein said medical image is a computed tomographic colonographic image.

* * * * *